US00PP08734P

United States Patent [19]

Fruehwirth

[11] Patent Number: Plant 8,734

[45] Date of Patent: May 17, 1994

[54] POINSETTIA PLANT "H-29"

[75] Inventor: Franz Fruehwirth, Encinitas, Calif.

[73] Assignee: Paul Ecke Ranch, Inc., Encinitas, Calif.

[21] Appl. No.: 59,614

[22] Filed: May 7, 1993

[51] Int. Cl.[5] ..... A01H 5/00

[52] U.S. Cl. ..... Plt./86.3

[58] Field of Search ..... Plt. 86.1, 86.3

*Primary Examiner*—James R. Feyrer

*Attorney, Agent, or Firm*—Arnold, White & Durkee

[57] ABSTRACT

Poinsettia "H-29" is a new cultivar, distinguished by peach pink bracts and unique flower bract formation and presentation. "H-29" is a seedling from cross pollination. The new plant produces a very desirable flowering pot plant. The post-production foliage and bract retention is excellent even under low light intensities in the consumer's home.

1 Drawing Sheet

BACKGROUND OF THE NEW PLANT

This new poinsettia cultivar, "H-29," originated as a seedling from cross pollination in my greenhouse in Encinitas, Calif., and was selected because of its unusual flower bract color, bract formation and bract presentation; traits which distinguish it from other poinsettia cultivars, and seem to make it a desirable plant for commercial greenhouse production. After selection, "H-29" was vegetatively reproduced from stem cuttings for test purposes in Encinitas, Calif. By subjecting clones of this plant to successive generations of vegetative propagation, it was demonstrated that the distinctive characteristics of "H-29" held true from generation to generation.

DESCRIPTION OF THE PHOTOGRAPHS

Poinsettia "H-29" is illustrated in the accompanying color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 unpinched plants per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Seedling from cross pollination. Parents were seedlings of unknown lineage.

Classification:

*Botanic.*—*Euphorbia pulcherrima* Willd.

*Common name.*—Poinsettia.

*Cultivar name.*—"H-29".

Form: Shrub.

Height: Short to medium.

Growth habit: As a single stemmed plant, upright and sturdy. The application of a chemical growth retardant may not be needed to restrict height for commercial pot plant production. I observed 3 single stem plants per pot with an overall height of 41 cm and an overall width of 42 cm. The bract diameter of individual flowers was 24 cm.

Branching: "H-29" is not a self-branching cultivar. However, if the terminal growing point is removed before flower induction, 4–5 axillary branches will develop at a uniform and fast rate, resulting in a very desirable branched flowering plant.

Growth rate: Rooting of stem cutting occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being 11–13 cm long and 10–11 cm wide with leaf petioles 5–6 cm long.

*Leaf shape.*—Typical leaves are generally ovate with acute to obtuse bases and acuminate tips. Leaf margins are notched and lobbed with 2 major lobes on each side of the leaf blade.

*Color.*—Upper side — Green, darker than RHS 137A. Under side — Green, between RHS 137B and RHS 137C.

*Retention.*—The foliage lasts extremely well even under low light intensities in the consumer's home.

Bracts: Generally there are 18–21 peach pink bracts of various sizes subtending the cyathia. The bract surface is uncommonly rugose and cupped downward at the margins. The bract petioles are often twisted. The bracts are held erect, some slightly below, but most above a horizontal plane. These features give depth to the bract presentation, as a whole. The primary bracts have blades typically 11–12 cm long and 10–11 cm wide with petioles about 1–2 cm long.

*Shape.*—Primary bracts are mostly ovate with acute bases and acuminate tips. Primary bracts are lobed with 1 or 2 indentations on either side of the bract. Secondary bracts are obovate to elliptic and have entire margins.

*Color.*—Upper side — The larger transitional and primary bracts are peach pink near RHS 24D. The intermediate sized, secondary bracts are bright pink near RHS 48C, but with veins of peach pink near RHS 24D. The smallest bracts nearest the center of the bract presentation are light orange, near RHS 24C. Under side — Peach pink. The patten of each color mirrors the upper surface. The pink of the primary bracts is near RHS 24D. The secondary bracts near RHS 48D, but with veins near RHS 24D. The smallest bracts near RHS 24D.

Flowers: Generally, 15–18 cyathia (flowers) are present when the plant is in full bloom. Each cyathium is about 7 mm long and 6 mm wide, green in color, and fringed with yellow at the distal end. Usually one, but often two yellow nectar cups protrude from the side of each cyathium. The flower pedicel is also green and about 5 mm in length. The stamens protruding from the cyathia are white. The anthers are bifurcate; the pollen is yellow. The stigmas are trifurcate.

Post production: "H-29" is resistant to epinasty. The leaves and bracts remain erect after being confined to shipping containers. The leaf and bract retention is excellent and the bracts do not fade or discolor.

What is claimed is:

1. A new and distinct Poinsettia cultivar, substantially as herein shown and described, distinguished by its unique peach pink flower bracts and unusual bract formation and presentation.

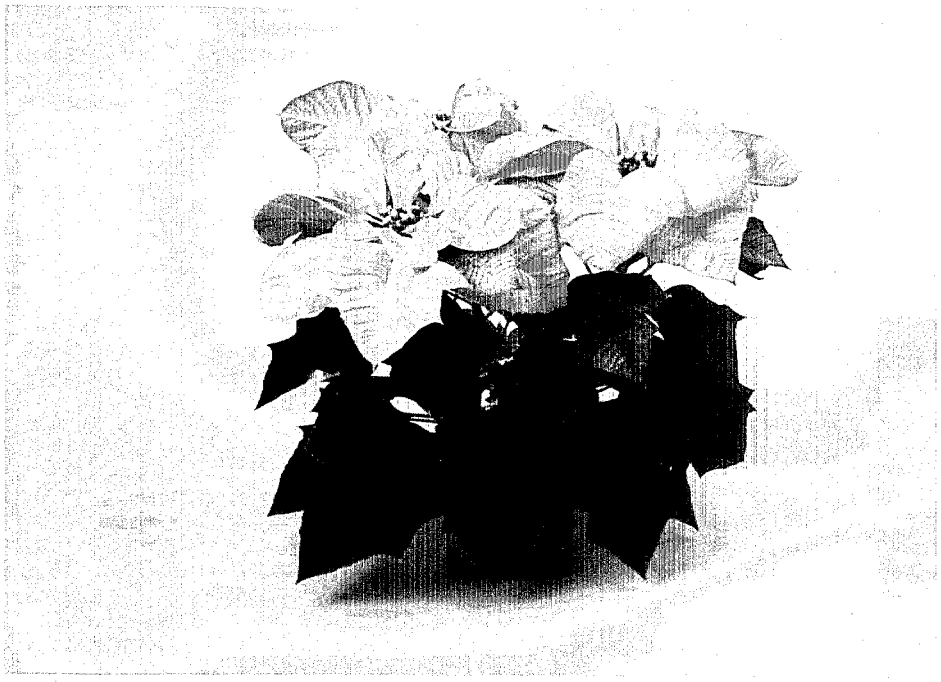
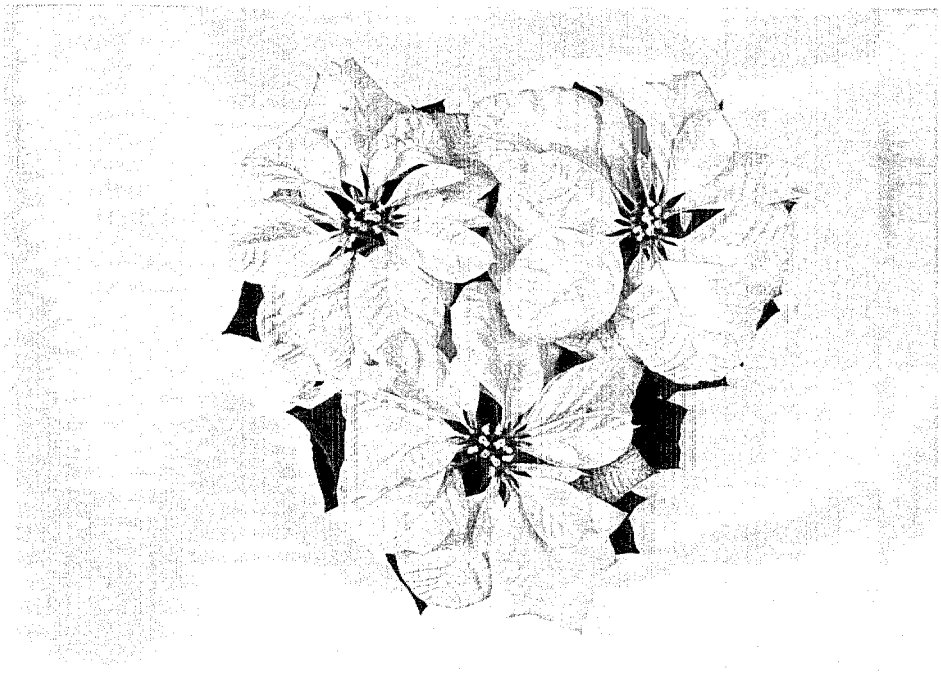

* * * * *